United States Patent
Lee et al.

(10) Patent No.: US 8,673,965 B2
(45) Date of Patent: Mar. 18, 2014

(54) COMPOSITION FOR THE TREATMENT OF ARTHRITIS CONTAINING A DIBENZO-P-DIOXIN DERIVATIVE AS THE ACTIVE INGREDIENT

(71) Applicant: Livechem, Inc., Jeju (KR)

(72) Inventors: Haeng Woo Lee, Seoul (KR); Hyeon Cheol Shin, Daejeon (KR); Seoung Ho Kim, Daejeon (KR); Yong Ju Park, Jeju-si (KR)

(73) Assignee: Livechem, Inc., Jeju, Jeju-Do (KR)

( * ) Notice: Subject to any disclaimer, the term of this patent is extended or adjusted under 35 U.S.C. 154(b) by 0 days.

(21) Appl. No.: 13/689,311

(22) Filed: Nov. 29, 2012

(65) Prior Publication Data

US 2013/0084330 A1 Apr. 4, 2013

Related U.S. Application Data

(63) Continuation of application No. 12/996,603, filed as application No. PCT/KR2009/002016 on Apr. 17, 2009, now abandoned.

(30) Foreign Application Priority Data

Jun. 5, 2008 (KR) .................. 10-2008-0053288

(51) Int. Cl.
*A01N 43/32* (2006.01)
*A61K 9/127* (2006.01)

(52) U.S. Cl.
USPC ........................................ 514/452; 424/450

(58) Field of Classification Search
None
See application file for complete search history.

(56) References Cited

FOREIGN PATENT DOCUMENTS

| KR | 10-2004-005710 A | 7/2004 |
| KR | 10-2008-0005711 A | 1/2008 |

OTHER PUBLICATIONS

Machine Translation of KR 20080005711 A published on Jan. 15, 2008 (14 total pages).*
Shin et al, "An Antioxidative and Antiinflammatory Agent for Potential Treatment of Osteoarthritis from Ecklonia cava," Arch. Pharm. Res., vol. 29, No. 2, pp. 165-171 (2006).*
Ahn, Ginnae, Immunomodulatory effects of Ecklonia cava, Feb. 2007, Master's thesis of Department of Marine Life Science, Cheju National University.
Bookman, Arthur A.M. et al., Effect of a topical diclofenac solution for relieving symptoms of primary osteoarthritis of the knee: a randomized controlled trial, Canadian Medical Association Journal, Aug. 17, 2004, vol. 171, Issue 4, pp. 333-338.
International Search Report dated Dec. 16, 2009, for International Application No. PCT/KR2009/002016.
McKenna, F. et al., Celecoxib versus diclofenac in the management of osteoarthritis of the knee, Scand J Rheumatology, 2001, vol. 30, pp. 11-18.
Shibata, Toshiyuki et al., Local and chemical distribution of phlorotannins in brown algae, Journal of Applied Phycology, 2004, vol. 16, Issue 291-296.
Simmonds, R.E. et al., Signalling, inflammation and arthritis: NF-KB and its relevance to arthritis and inflammation, Rheumatology, 2008, vol. 47, pp. 584-590.
Sugiura, Yoshimasa et al., Inhibitory effects of seaweeds on histamine release from rat basophile leukemia cells (RBL-2H3), Fisheries Science, 2006, vol. 72, pp. 1286-1291.
Shibata, et al., Antioxidant Activities of Phloratannins Isolated from Japanese Laminariaceae, J. App. Phycol., vol. 20, No. 5, pp. 705-711 (2008; published online on Oct. 6, 2007).

* cited by examiner

*Primary Examiner* — Frederick Krass
*Assistant Examiner* — Dennis J Parad
(74) *Attorney, Agent, or Firm* — Knobbe, Martens, Olson & Bear, LLP

(57) ABSTRACT

Disclosed is a composition for treating arthritis containing a dibenzo-p-dioxin derivative as an active ingredient. This dibenzo-p-dioxin derivative is very effective in inhibiting NF-kB and AP-1 activity, alleviates the symptoms of degenerative arthritis and rheumatoid arthritis without irritating the skin or causing side effects, and can continue to exhibit improvement effects for a considerable period of time after discontinuation of treatment. Additionally, when the dibenzo-p-dioxin derivative is contained in liposomes, the composition of the invention exhibits much greater effects on treating arthritis by absorption through skin, and thus is useful for the treatment of degenerative arthritis and rheumatoid arthritis.

8 Claims, No Drawings

COMPOSITION FOR THE TREATMENT OF ARTHRITIS CONTAINING A DIBENZO-P-DIOXIN DERIVATIVE AS THE ACTIVE INGREDIENT

TECHNICAL FIELD

The present invention relates to a composition for treating arthritis, which contains a dibenzo-p-dioxin derivative as an active ingredient.

BACKGROUND ART

Arthritis is largely classified into degenerative arthritis (osteoarthritis) and rheumatoid arthritis. Degenerative arthritis, called osteoarthritis, is a disease which is very common and mainly occurs in middle or old age and also which causes pain, stiffness and restriction at the joints to which a high body weight is applied, such as the knee joint and the hip joint. Arthritis, which was simply regarded in the past as a sign of the aging process, is currently considered to have symptoms that vary depending on various factors such as age, inheritance, obesity, shape of joints, hormones, etc. Degenerative arthritis is known to be mainly caused by gradual damage done to the articular cartilage which causes chronic inflammation which is then accompanied by the degeneration of peripheral tissue. Specifically, as physical stress accumulates on the cartilage tissue, transcription factors such as NF-kB and AP-1 are activated in the cartilage tissue, undesirably causing chronic inflammation. When this happens, factors for mediating and amplifying the inflammation, such as COX-2, LOX and the like, are expressed, peripheral blood circulation is suppressed, and tissue degrading factors such as matrix metalloproteinases (MMPs), hyaluronidase, iNOS and the like are over-expressed, thus degenerating the cartilage tissue to thereby affect peripheral tissue such as muscles, tendons, and ligaments, resulting in severe pain.

On the other hand, rheumatoid arthritis is an inflammatory self-immune disease which occurs at multiple joints. The synovial tissue and synovia of the patient suffering from rheumatoid arthritis may cause chronic inflammation by excessive action of inflammatory cells (macrophages, T-cells, B-cells, dendritic cells, etc.), thus damaging the joints and cartilage and inducing pain.

As mentioned above, the tissue affected by degenerative arthritis or rheumatoid arthritis involves chronically elevated levels of inflammatory mediators such as COX, LOX, iNOS and the like, and also involves the overly activated MMP enzymes that decompose the tissue. Conventionally, drugs for suppressing such factors or methods of inhibiting activities of tissue-decomposing enzymes resulting from inflammatory reactions have been used. The current major drugs used to treat degenerative arthritis and rheumatoid arthritis are non-steroidal anti-inflammatory drugs (NSAIDs). These NSAIDs slightly improve the symptoms but cannot block the loss of cartilage around the joint or the progress of the disease, and may cause severe side effects. For these reasons, about a half the patients under treatment using these drugs should discontinue the treatment within one year. The NSAID therapy which suppresses the biochemical processes related with the symptoms rather than with the causes of arthritis is problematic because its side effects outbalance its efficacy.

The upstream factors to the chronic activation of the inflammatory mediators such as COX, LOX, iNOS and the like include NF-kB and AP-1. These transcription factors are underlying and common causes of degenerative and rheumatoid arthritis, and function to obstruct the healing of the damaged tissue by compromising the process for replacing abnormal cells with new cells (Simmonds, R. E. & Foxwell, B. M. Rheumatology Advance Access published Jan. 29, 2008).

The conventional treatments are problematic because they focus only on pain suppression by inhibiting the acute inflammatory reaction and do not fundamentally treat the chronic inflammation and degeneration of tissue. Even in inhibiting the acute inflammation and pain, oral administration of current NSAIDs cause serious side effects such as gastrointestinal bleeding or thrombosis. These problems have led to widespread use of their local application using patch type of products. However, their pain-relieving effects are only temporary and do not significantly contribute to improvement in quality of life of the patients.

Hence, there is a need for the development of drugs which have both safety and fundamental treatment effects for degenerative arthritis and rheumatoid arthritis by inhibiting over-expression of NF-kB and AP-1.

DISCLOSURE

Technical Problem

While investigating the potential chemicals capable of effective inhibition of over-expression of NF-kB and AP-1 that are fundamentally responsible for degenerative arthritis and rheumatoid arthritis, the present inventors have discovered that dibenzo-p-dioxin derivatives effectively inhibit the over-expression of NF-kB and AP-1 and offer anti-arthritic effects for a considerable period of time even after discontinuation of treatment, thus completing the present invention.

Technical Solution

The present invention is intended to provide a composition for treating arthritis containing a dibenzo-p-dioxin derivative as an active ingredient.

BEST MODE

The present invention provides a composition for treating arthritis, containing, as an active ingredient, one or more selected from the group consisting of dibenzo-p-dioxin derivatives of Formulas 1 to 10 below.

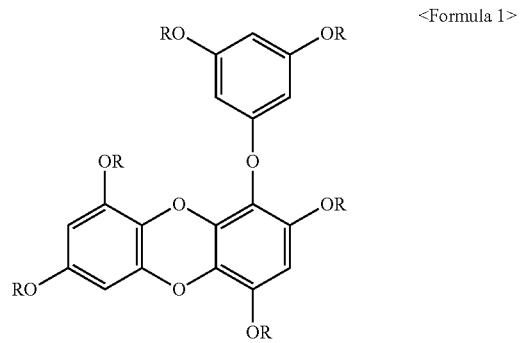

<Formula 1>

<Formula 2>
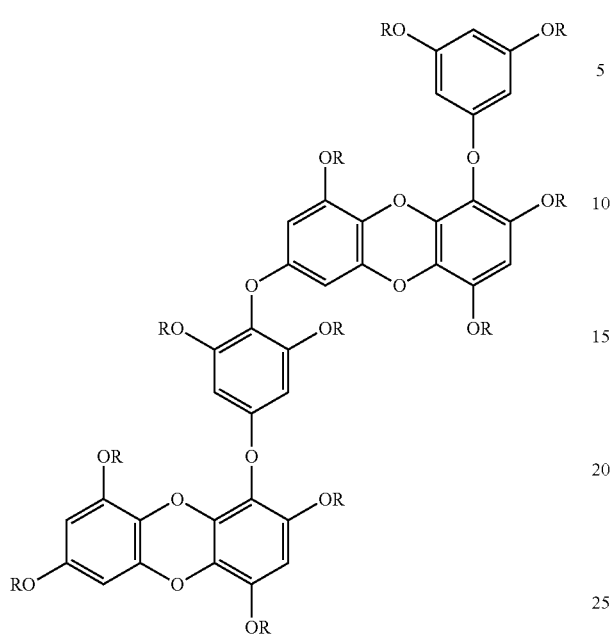
<Formula 3>
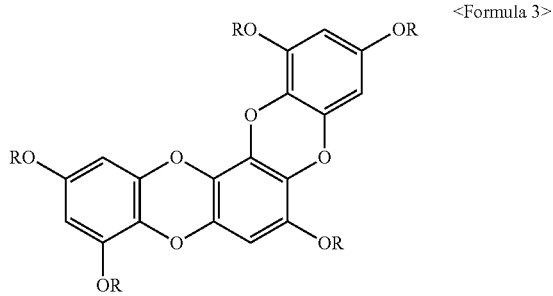
<Formula 4>
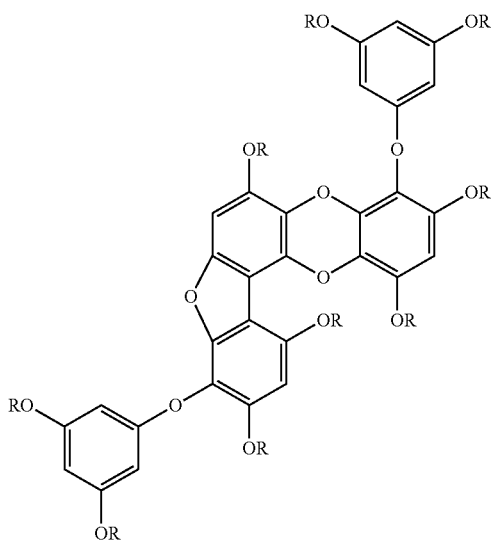
<Formula 5>
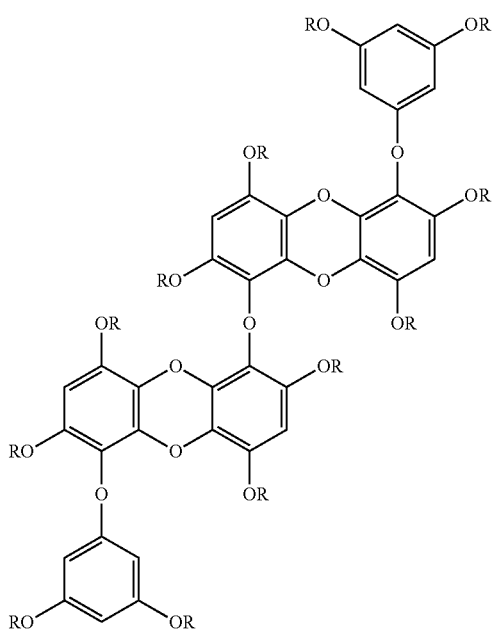
<Formula 6>
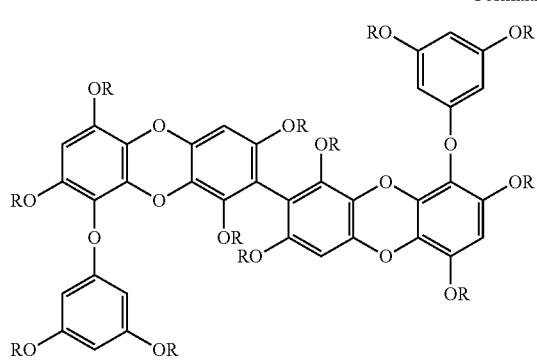
<Formula 7>
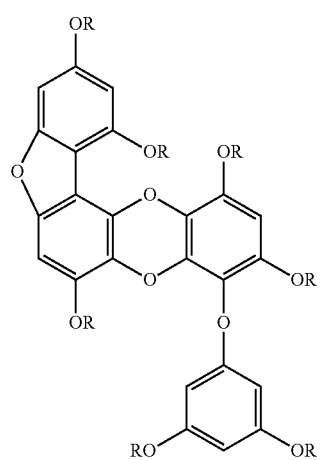

-continued

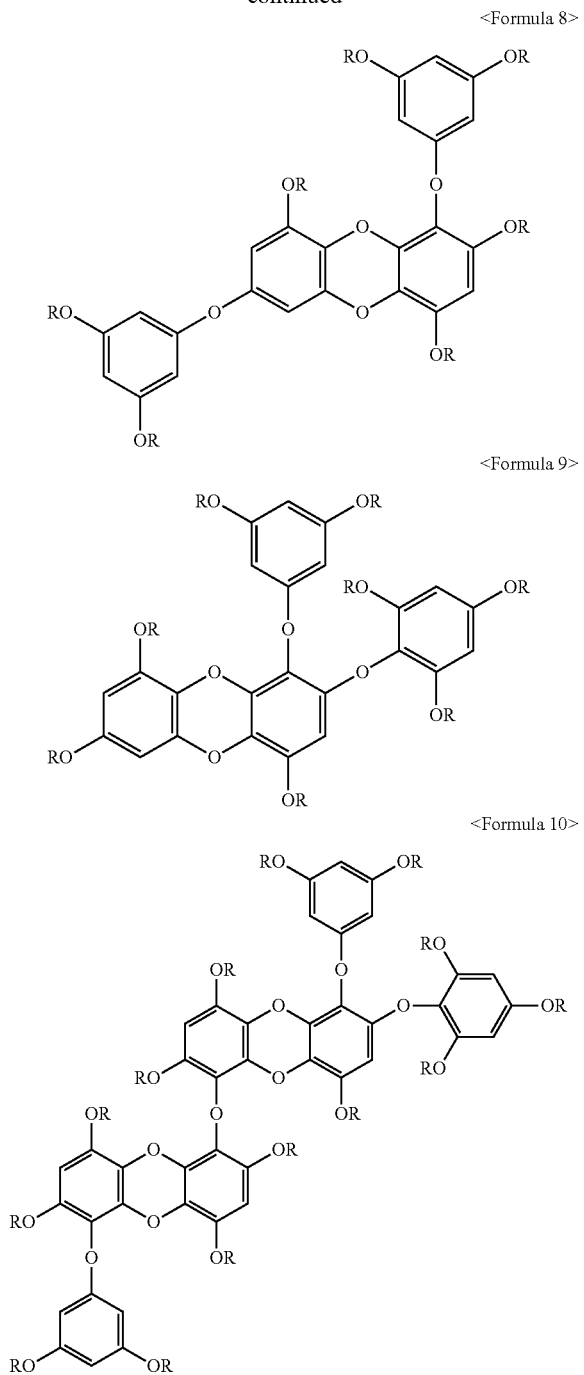

<Formula 8>

<Formula 9>

<Formula 10>

In Formulas 1 to 10, each R is independently hydrogen, $C_1$~$C_4$ alkyl, $C_2$~$C_{10}$ alkenyl, phenyl, hydroxyphenyl, dihydroxyphenyl, phenyl-$C_1$~$C_4$ alkyl or R'(C=O) in which R' is $C_1$~$C_4$ alkyl or $C_2$~$C_{20}$ alkenyl.

Preferably in Formulas 1 to 10, each R is independently hydrogen, methyl, acetyl or oleoyl.

More preferably in Formulas 1 to 10, each R is independently hydrogen.

The composition according to the present invention may include a combination of two or more out of dibenzo-p-dioxin derivatives of Formulas 1 to 10. For example, two or more compounds selected from the group consisting of 0.1~10 wt % of a compound of Formula 1, 1~60 wt % of a compound of Formula 2, 1~20 wt % of a compound of Formula 3, 0.2~20 wt % of a compound of Formula 4, 0.3~30 wt % of a compound of Formula 5, 0.3~30 wt % of a compound of Formula 6, 0.1~10 wt % of a compound of Formula 7, 0.1~10 wt % of a compound of Formula 8, 0.1~10 wt % of a compound of Formula 9 and 0.2~20 wt % of a compound of Formula 10 may be combined and used.

The dibenzo-p-dioxin derivatives of Formulas 1 to 10 may be obtained by being extracted and separated from one or more sea algae selected from the group consisting of *Eisenia bicyclis, Eisenia arborea, Eisenia desmarestioides, Eisenia galapagensis, Eisenia masonii, Ecklonia kurome, Ecklonia cava, Ecklonia stolonifera, Ecklonia maxima, Ecklonia radiata, Ecklonia bicyclis, Ecklonia biruncinate, Ecklonia buccinalis, Ecklonia caepaestipes, Ecklonia exasperta, Ecklonia fastigiata, Ecklonia brevipes, Ecklonia arborea, Ecklonia latifolia, Ecklonia muratii, Ecklonia radicosa, Ecklonia richardiana* and *Ecklonia wrightii*. Preferably, the dibenzo-p-dioxin derivatives of Formulas 1 to 10 may be obtained by being extracted and separated from one or more sea algae selected from the group consisting of *Eisenia bicyclis, Ecklonia cava, Ecklonia kurome* and *Ecklonia stolonifera*.

Hereinafter, a detailed description will be given of the present invention.

According to the present invention, the dibenzo-p-dioxin derivatives may be obtained by all typical methods, may be prepared by using commercially available reagents, and may be obtained by being extracted and separated from sea algae. In the present invention, the dibenzo-p-dioxin derivatives are prepared by extraction and separation as described below.

Specifically, sea algae are washed with distilled water to remove impurities, dried in the shade and then ground. The above sea algae are extracted under reflux condition (two repetitions) with 20 parts of water, a $C_1$~$C_4$ lower alcohol or solvent mixtures thereof, preferably ethanol. The extract is concentrated under reduced pressure, suspended in 20 parts of distilled water, and then extracted three times with the same amount of ethylacetate solvent to thus collect an ethylacetate fraction which is then concentrated under reduced pressure. The concentrated ethylacetate fraction is separated into ten active materials using silica gel column chromatography and high-performance liquid chromatography (HPLC). Respective compounds are confirmed to be dibenzo-p-dioxin derivatives of Formulas 1 to 10.

The dibenzo-p-dioxin derivatives of Formulas 1 to 10 may be used in the form of a pharmaceutically acceptable salt, and may include all salts, ester derivatives, hydrates and solvates, which are prepared using typical methods. Useful as the above salt is an acid addition salt formed by a pharmaceutically acceptable free acid. The free acid may include an inorganic acid and an organic acid, and examples of the inorganic acid include hydrochloric acid, bromic acid, sulfuric acid, and phosphoric acid, and examples of the organic acid include citric acid, acetic acid, lactic acid, maleic acid, umaric acid, gluconic acid, methanesulfonic acid, glyconic acid, succinic acid, 4-toluenesulfonic acid, trifluoroacetic acid, galacturonic acid, embonic acid, glutamic acid or aspartic acid.

According to the present invention, the dibenzo-p-dioxin derivatives are very effective in inhibiting NF-kB and AP-1 activity, and are able to alleviate the symptoms of degenerative arthritis and rheumatoid arthritis without irritating the skin or causing side effects, and also may continue to exhibit improvement effects for a considerable period of time after discontinuation of the treatment. In particular, a liposome composition containing the dibenzo-p-dioxin derivative according to the present invention is superior in terms of maximum effect during treatment, total treatment effect, and healing effect upon discontinuation of treatment, compared with the non-liposomic external-use composition containing the dibenzo-p-dioxin derivative. Moreover, a SUV type liposome composition may exhibit effects that are much superior to those of other liposome compositions (MLV, LUV) and non-liposomic external-use compositions. Thus, the composition according to the present invention may exhibit much higher effects on treating arthritis through skin by containing the dibenzo-p-dioxin derivative in the liposome, and is thus useful in treating degenerative arthritis and rheumatoid arthritis.

The composition according to the present invention may include about 0.2~2 wt %, preferably about 0.5~1.5 wt % of the dibenzo-p-dioxin derivative based on the weight of the composition.

The composition according to the present invention may include not only the aforementioned active ingredient but also one or more pharmaceutically acceptable carriers and thus may be prepared in the form of a local formulation, in order for it to be administered. The pharmaceutically acceptable carrier may include saline, sterile water, linger liquid, buffer saline, a dextrose solution, a malto dextrin solution, glycerol, ethanol and mixtures of one or more thereof, and also may include an additive such as an antioxidant, a buffer, a bacteriostatic agent or the like, as necessary. Furthermore, a diluent, a dispersant, a surfactant, a binder and a lubricant may be added, and thus the composition according to the present invention may be typically prepared in the form of a local formulation such as an ointment, lotion, cream, gel, skin emulsion, skin suspension, patch or spray. In addition, the composition according to the present invention may be provided in the form of a liposome formulation using liposomes. Furthermore, the composition may be formulated so as to be adapted for respective diseases or components using a typical method in the art or a method disclosed in Remington's Pharmaceutical Science (recent publication), Mack Publishing Company, Easton Pa. The composition according to the present invention may be administered in a dose range varying depending on the patient's body weight, age, gender, health condition, diet, administration time, administration method, excretion rate and disease severity. The composition according to the present invention may be applied in a dose of 1~1000 μg/cm² per day, preferably 5~500 μg/cm² per day, and may be applied one time to five times per day for one month or longer.

MODE FOR INVENTION

A better understanding of the present invention is furnished by the following examples which are set forth to illustrate, but are not to be construed as limiting the present invention.

Example 1

Separation of Dibenzo-p-Dioxin Derivative from Sea Algae

1. Preparation of Sea Algae Extract

*Ecklonia cava* and *Eisenia bicyclis* were washed with distilled water to remove impurities, dried in the shade and then ground. 500 g of a mixture of *Ecklonia cava* and *Eisenia bicyclis* (350 g of *Ecklonia cava* and 150 g of *Eisenia bicyclis*) was reflux extracted for 2 hours using 20 parts of 10% ethylalcohol. This extraction procedure was repeated two times. Thereafter, the residue was filtered and removed and the ethylalcohol extract was concentrated under reduced pressure using a rotary evaporator. The concentrate was suspended in 20 parts of distilled water, and extracted three times using the same amount of ethylacetate solvent, thus collecting an ethylacetate fraction which was then concentrated under reduced pressure. The concentrated ethylacetate fraction was loaded on 15 parts of silica gel and then fractions in which active ingredients were dissolved were collected using a solvent mixture of ethylacetate/acetone (volume ratio: 9/1) and concentrated, thus obtaining a sea algae extract.

2. Separation of Active Materials from Sea Algae Extract

The above sea algae extract was filtered using 0.2 μm membrane filter and then loaded on HPLC. In the HPLC, a HP ODS Hypersil column was used and distilled water and methanol were used as a solvent, and the solvent was supplied in a flow rate of 1.0 mL/min at a linear methanol gradient from 15% to 70% over 30 min, so that ten active materials were separated. Respective compounds were confirmed to be dibenzo-p-dioxin derivatives of Formulas 1 to 10 below.

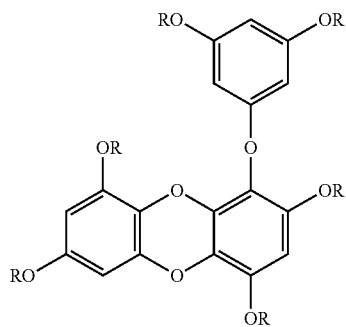

<Formula 1>

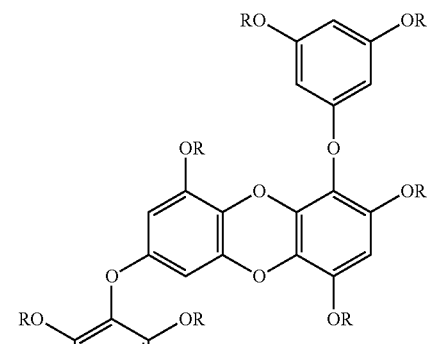

<Formula 2>

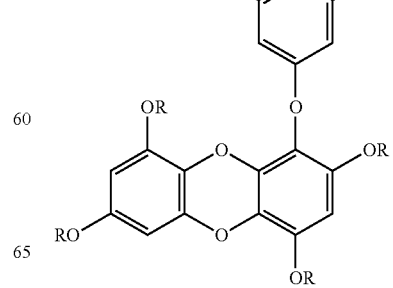

<Formula 3>
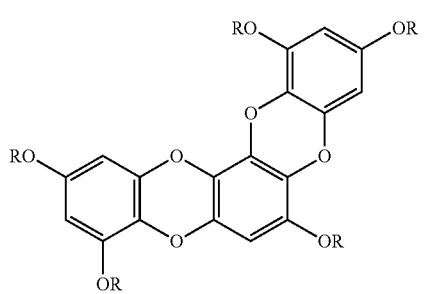
<Formula 4>
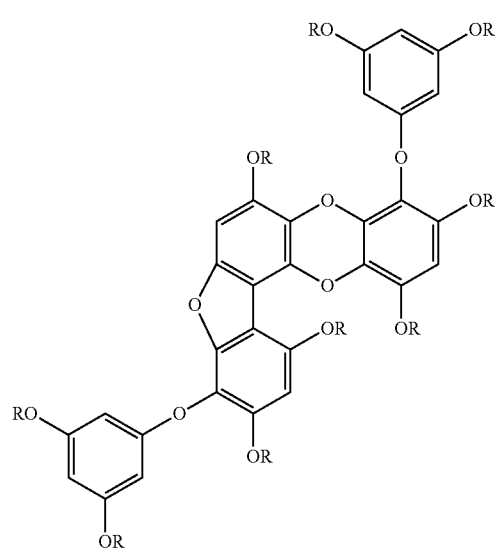
<Formula 5>
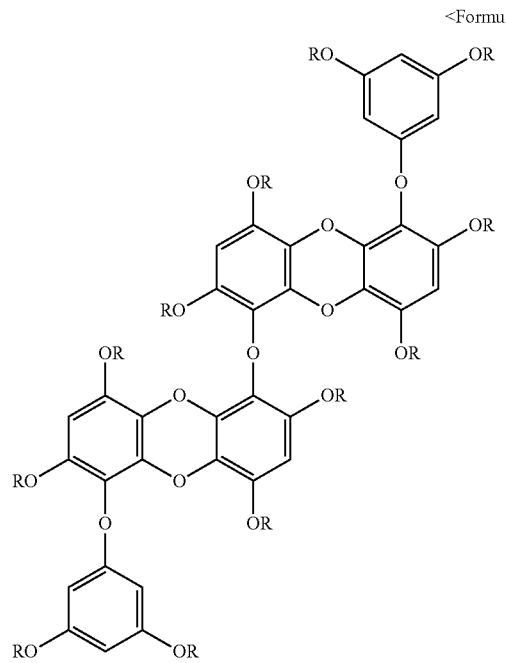
<Formula 6>
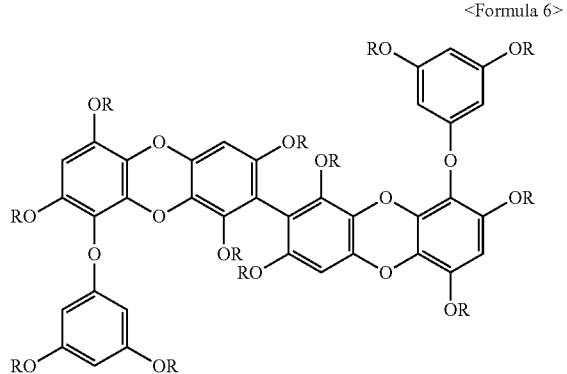
<Formula 7>
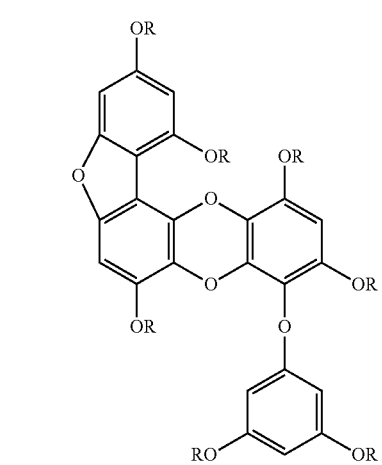
<Formula 8>
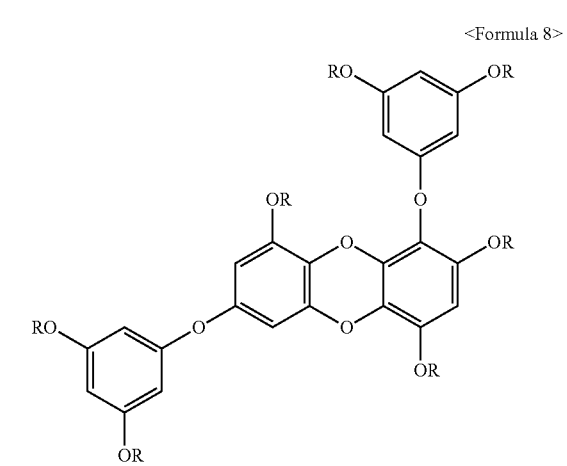
<Formula 9>
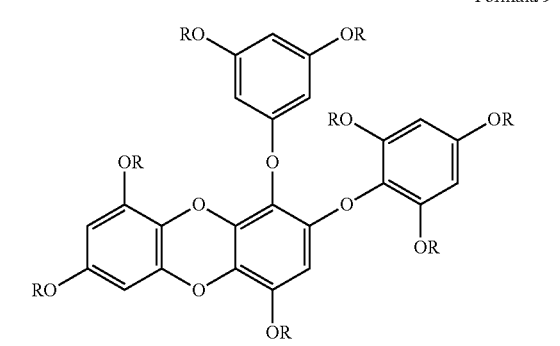

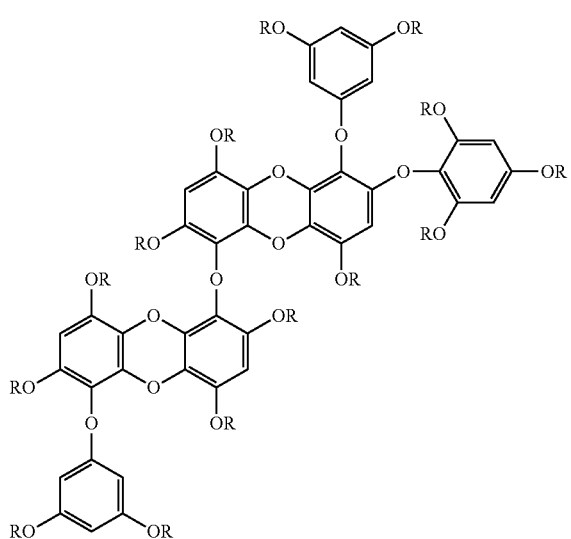

<Formula 10>

In Formulas 1 to 10, each R is independently hydrogen, methyl, acetyl or oleoyl.

Experimental Example 1

Effects of Dibenzo-p-Dioxin Derivatives According to the Present Invention on Inhibiting NF-kB and AP-1 Activity In order to evaluate the effects of the dibenzo-p-dioxin derivatives according to the present invention on inhibiting NF-kB and AP-1 activity, the following test was conducted.

The dibenzo-p-dioxin derivatives of Formulas 1 to 10 separated in Example 1 were used alone or in combinations of two or more for tests. Respective sample compositions are shown in Table 1 below. As controls, anti-inflammatory agents mainly used for treating arthritis, for example, aspirin, dichlofenac, ibuprofen, celecoxib, indomethacin, and ketoprofen, were used.

TABLE 1

| Sample | Sample Composition |
|--------|---------------------|
| 1 | Formula 1 (R = H) 100% |
| 2 | Formula 2 (R = H) 100% |
| 3 | Formula 3 (R = H) 100% |
| 4 | Formula 4 (R = H) 100% |
| 5 | Formula 5 (R = H) 100% |
| 6 | Formula 6 (R = H) 100% |
| 7 | Formula 7 (R = H) 100% |
| 8 | Formula 8 (R = H) 100% |
| 9 | Formula 9 (R = H) 100% |
| 10 | Formula 10 (R = H) 100% |
| 11 | Formula 2 (R = H) 60% + Formula 3 (R = H) 25% + Formula 4 (R = H) 15% |
| 12 | Formula 4 (R = H) 70% + Formula 5 (R = H) 8% + Formula 6 (R = H) 22% |
| 13 | Formula 4 (R = H) 10% + Formula 10 (R = H) 80% + Formula 7 (R = H) 10% |
| 14 | Formula 1 (R = H) 3% + Formula 2 (R = H) 37% + Formula 3 (R = H) 4% + Formula 4 (R = H) 6% + Formula 5 (R = H) 25% + Formula 6 (R = H) 25% |
| 15 | Formula 2 (R = H) 60% + Formula 4 (R = H) 20% + Formula 6 (R = H) 15% + Formula 7 (R = H) 5% |
| 16 | Formula 4 (R = Acetyl, H (3:7)) 100% |
| 17 | Formula 2 (R = Oleoyl, H (1:9)) 100% |
| 18 | Formula 6 (R = Methyl, H (2:8)) 100% |

A five-week-old rabbit was killed, from the hock joint of which the articular cartilage was then taken. The articular surface (200~220 mg/joint) was placed in a complete medium (DMEM, supplemented with heat inactivated 5% FBS; penicillin 100 U/mL; streptomycin 100 μg/mL) under sterile conditions. It was washed three or four times and then incubated at 37° C. for about 1~2 days under sterile conditions and under 5% $CO_2$/95% air conditions, after which AP-1-luciferase or NFkB-luciferase reporter plasmid DNA (each 0.5 μg: Stratagene) was transfected into the incubated tissue using a Lipofectamin transfection reagent (Invitrogen, Carlsbad, Calif., U.S.A.). After 24 hours, the complete medium was exchanged with a basic medium (DMEM, supplemented with heat inactivated 1% FBS, 10 mM HEPES, penicillin 100 U/mL, streptomycin 100 μg/mL). The incubated cartilage tissue (50~60 mg) was aliquoted into a 96-well plate, and samples 1~18 and controls (aspirin, dichlofenac, ibuprofen, celecoxib, indomethacin, ketoprofen) were treated at a concentration of 10 μg/mL. After 1 hour, the culture medium of each group was treated with 5 ng/mL rhIL-1α (R&D systems, Minneapolis, USA). Then, the culture medium was incubated at 7° C. under 5% $CO_2$/95% air conditions for 60 hours, and then treated with a lysis buffer (0.1M potassium phosphate buffer, pH 7.8/1% Triton X-100/1 mM DTT/2 mM EDTA), and the luciferase activity in the culture medium was measured using a luminometer (Monolight 2010). The results are shown in Table 2 below.

TABLE 2

| Sample | NF-kB Activity Inhibition (%) | AP-1 Activity Inhibition (%) |
|--------|------|------|
| 1 | 53 | 65 |
| 2 | 73 | 57 |
| 3 | 75 | 78 |
| 4 | 65 | 72 |
| 5 | 61 | 75 |
| 6 | 66 | 66 |
| 7 | 62 | 60 |
| 8 | 67 | 57 |
| 9 | 75 | 60 |
| 10 | 64 | 71 |
| 11 | 70 | 69 |
| 12 | 73 | 80 |
| 13 | 71 | 74 |
| 14 | 82 | 77 |
| 15 | 76 | 52 |
| 16 | 55 | 52 |
| 17 | 64 | 51 |
| 18 | 69 | 55 |
| Aspirin | 48 | 46 |
| Dichlofenac | 32 | 34 |
| Ibuprofen | 23 | 27 |
| Celecoxib | 10 | 23 |
| Indomethacin | 18 | 34 |
| Ketoprofen | 12 | 22 |

As is apparent from Table 2, the NF-kB and AP-1 activity inhibitions by the dibenzo-p-dioxin derivatives according to the present invention can be seen to be 53~82% and 51~80%, respectively, but to be 10~48% and 22~46% respectively by the controls. Thus, the dibenzo-p-dioxin derivatives according to the present invention can be confirmed to be very effective in inhibiting NF-kB and AP-1 activity.

Experimental Example 2

Effects of External-Use Composition Containing Dibenzo-p-Dioxin Derivative According to the Present Invention on Treating Arthritis in the Arthritis Induced Rabbit (in Vivo)

In order to evaluate the effects of an external-use composition containing the dibenzo-p-dioxin derivative according to the present invention on treating arthritis in an arthritis induced rabbit, the following test was performed.

Samples 12 and 14 having the highest NF-kB and AP-1 activity inhibitions and aspirin and dichlofenac controls having superior inhibitory effects in Experimental Example 1 were selected and used to prepare external-use compositions. The composition of a carrier used to absorb the active ingredient into the skin was made referring to Bookman et al (Can. Med. Assoc. J. 171(4) 333-338 (2004)). The components of respective external-use compositions are shown in Table 3 below.

TABLE 3

|  | Carrier | Aspirin | Dichlofenac Sodium | Sample 12 | Sample 14 |
| --- | --- | --- | --- | --- | --- |
| DMSO | 45.5% | 45.5% | 45.5% | 45.5% | 45.5% |
| Propyleneglycol | 5.0% | 5.0% | 5.0% | 5.0% | 5.0% |
| Glycerin | 5.0% | 5.0% | 5.0% | 5.0% | 5.0% |
| Ethylalcohol | 8.0% | 8.0% | 8.0% | 8.0% | 8.0% |
| Distilled Water | 36.5% | 35.0% | 35.0% | 35.0% | 35.0% |
| Corresponding Active Ingredient | 0% | 1.5% | 1.5% | 1.5% | 1.5% |
| Total | 100.0% | 100.0% | 100.0% | 100.0% | 100.0% |

In order to induce arthritis in the rabbit, six test groups were set up, and five rabbits were randomly assigned into each group. A collagenase solution (4 mg/mL, saline) was filtered with a 0.22 µm membrane. 2.5~3.0 kg weighed rabbits assigned into six test groups were anesthetized with tiletamine-zolazepam (Zoletil 50, Virbac, France). The region around the right knee joint of each rabbit was shaved and disinfected, after which the articular cavity thereof was injected with 0.25 mL of saline in one test group and 0.25 mL of the collagenase solution in the other five test groups (Choi, et al. Osteoarthritis and Cartilage 10, 471-478 (2002)). After 7 days, the test group treated with saline did not show knee arthritis symptoms and the test groups treated with the collagenase solution showed peak arthritic symptoms. This model has been adopted because it is similar to the degeneration of the cartilage tissue in the human degenerative arthritis.

From the $7^{th}$ day, 0.3 mL of each of the external-use compositions of Table 3 was sufficiently applied two times per day for 7 days to the affected part of the five test groups treated with the collagenase solution, and no treatment was performed for the following 7 days in order to evaluate the fundamental healing effects. The swelling, reddening, heat and limping of the articular part were quantitatively evaluated on the day ($0^{th}$ day) immediately before collagenase treatment, the $7^{th}$ day, the $14^{th}$ day and the $21^{st}$ day, using the evaluation criteria comprising 0 (normal), 1 (low), 2 (middle), 3 (high). In order to objectively evaluate the effects of respective treatment solutions, the total score at each evaluation was compared, and "maximum effect during treatment", "total treatment effect", "healing effect upon discontinuation of treatment" were calculated by the following equations. The results are shown in Table 4 below.

(1) Maximum effect during treatment=(total score on $7^{th}$ day−total score on $14^{th}$ day)/total score on $7^{th}$ day, (2) Total treatment effect=(total score on $7^{th}$ day−total score on $21^{st}$ day)/total score on $7^{th}$ day, (3) Healing effect upon discontinuation of treatment=(total score on $14^{th}$ day−total score on $21^{st}$ day)/total score on $14^{th}$ day.

TABLE 4

| Evaluation Item | | Carrier | Aspirin | Dichlofenac Sodium | Sample 12 | Sample 14 |
| --- | --- | --- | --- | --- | --- | --- |
| Swelling | $7^{th}$ Day | 2.8 ± 0.45 | 3.0 ± 0.00 | 2.8 ± 0.45 | 2.8 ± 0.45 | 2.8 ± 0.45 |
|  | $14^{th}$ Day | 2.4 ± 0.55 | 1.6 ± 0.55 | 1.4 ± 0.55 | 1.2 ± 0.45 | 1.0 ± 0.00 |
|  | $21^{st}$ Day | 1.6 ± 0.55 | 1.2 ± 0.45 | 1.4 ± 0.55 | 0.6 ± 0.55 | 0.6 ± 0.55 |
| Reddening | $7^{th}$ Day | 3.0 ± 0.00 | 2.8 ± 0.45 | 2.8 ± 0.45 | 3.0 ± 0.00 | 3.0 ± 0.00 |
|  | $14^{th}$ Day | 2.4 ± 0.55 | 1.6 ± 0.55 | 1.4 ± 0.55 | 1.4 ± 0.55 | 1.2 ± 0.45 |
|  | $21^{st}$ Day | 1.6 ± 0.55 | 1.4 ± 0.55 | 1.4 ± 0.55 | 0.8 ± 0.45 | 0.4 ± 0.55 |
| Heating | $7^{th}$ Day | 2.8 ± 0.45 | 3.0 ± 0.00 | 2.8 ± 0.45 | 2.8 ± 0.45 | 3.0 ± 0.00 |
|  | $14^{th}$ Day | 2.2 ± 0.45 | 1.4 ± 0.55 | 1.4 ± 0.55 | 1.0 ± 0.71 | 1.0 ± 0.71 |
|  | $21^{st}$ Day | 1.6 ± 0.55 | 1.2 ± 0.45 | 1.2 ± 0.45 | 0.6 ± 0.55 | 0.6 ± 0.55 |
| Limping | $7^{th}$ Day | 3.0 ± 0.00 | 2.8 ± 0.45 | 3.0 ± 0.00 | 3.0 ± 0.00 | 2.8 ± 0.45 |
|  | $14^{th}$ Day | 2.6 ± 0.55 | 1.4 ± 0.55 | 1.6 ± 0.55 | 0.6 ± 0.55 | 0.6 ± 0.55 |
|  | $21^{st}$ Day | 1.8 ± 0.45 | 1.2 ± 0.45 | 1.4 ± 0.55 | 0.4 ± 0.55 | 0.2 ± 0.45 |
| Total Score | $7^{th}$ Day | 11.6 ± 0.55 | 11.6 ± 0.89 | 11.4 ± 1.34 | 11.6 ± 0.89 | 11.6 ± 0.55 |
|  | $14^{th}$ Day | 9.6 ± 0.55 | 6.0 ± 0.71 | 5.8 ± 1.3 | 4.2 ± 1.3 | 3.8 ± 0.84 |
|  | $21^{st}$ Day | 6.6 ± 0.89 | 5.0 ± 1.0 | 5.4 ± 0.55 | 2.4 ± 1.14 | 1.8 ± 1.48 |
| Max. Effect during Treatment | | 17.2% | 48.3% | 49.1% | 63.8% | 67.2% |
| Total Treatment Effect | | 43.1% | 56.9% | 52.6% | 79.3% | 84.5% |
| Healing Effect upon Discontinuation of Treatment | | 31.3% | 16.7% | 6.9% | 42.9% | 52.6% |

As is apparent from Table 4, the external-use compositions containing the dibenzo-p-dioxin derivative according to the present invention exhibited much higher efficacy than those containing aspirin or dichlofenac sodium in the maximum treatment effect during treatment, total treatment effect, and healing effect upon discontinuation of treatment, and in particular, those containing the dibenzo-p-dioxin derivative according to the present invention exhibited about 3~7 times higher efficacy in terms of the healing effect upon discontinuation of treatment.

Experimental Example 3

Effects of Liposome Composition Containing Dibenzo-p-Dioxin Derivative According to the Present Invention on Treating Arthritis in the Arthritis Induced Rabbit (In Vivo)

In order to evaluate the effects of a liposome composition containing the dibenzo-p-dioxin derivative according to the present invention on treating arthritis in an arthritis induced rabbit, the following test was conducted.

1. Preparation of Liposome Composition

Various liposomes of sample 14 which showed the greatest effects in Experimental Examples 1 and 2 were prepared, in order to develop a composition according to the present invention that is more readily absorbed through the skin to reach the arthritis-affected tissue and exert an effective therapeutic effect.

72 g of a lipid (egg yolk lecithin or soybean lecithin: cholesterol=15:3) was added to 2 L of distilled water, stirred at 75° C. for 30 min and thus uniformly dispersed, mixed with 2 L of an aqueous solution (including 0.5 wt % of sample 14) at 75° C., stirred at 4000 rpm at 75° C. for 5 min and cooled to room temperature. Thereby, multi-lamella vesicles (MLV) were primarily formed. Then, MLV was placed into an ice bath and sonicated for a predetermined period of time, thus preparing small unilamella vesicles (SUV). Furthermore, SUV was repetitively lyophilized thus obtaining large unilamella vesicles (LUV). The size of the prepared liposomes was measured using light scattering (ZetaPALS Particle Sizing Analyzer, Brookhaven Instrument Corporation). The results are shown in Table 5 below.

TABLE 5

| Type of Liposome | Egg Yolk Lecithin | Soybean Lecithin |
|---|---|---|
| MLV | 850 nm | 1850 nm |
| SUV | 60 nm | 30 nm |
| LUV | 840 nm | 500 nm |

2. Effects of Liposome Composition In Vivo

The liposome composition made with soybean lecithin (including 0.5 wt % of sample 14) prepared as above were evaluated on arthritic treatment effect. For comparison, an external-use composition was prepared in the same manner as in Experimental Example 2 using 1.5 wt % of sample 14. The evaluation method was the same as in Experimental Example 2. The results are shown in Table 6 below.

TABLE 6

| Evaluation Item | | Liposome Composition | | | External-Use Composition |
|---|---|---|---|---|---|
| | | MLV | SUV | LUV | (Sample 14) |
| Swelling | 7th Day | 3.0 ± 0.00 | 2.8 ± 0.45 | 2.8 ± 0.45 | 2.8 ± 0.45 |
| | 14th Day | 2.2 ± 0.45 | 1.0 ± 0.00 | 1.4 ± 0.55 | 1.6 ± 0.55 |
| | 21st Day | 0.6 ± 0.55 | 0.4 ± 0.55 | 0.6 ± 0.55 | 1.0 ± 0.00 |
| Reddening | 7th Day | 2.8 ± 0.45 | 3.0 ± 0.00 | 3.0 ± 0.00 | 3.0 ± 0.00 |
| | 14th Day | 1.6 ± 0.55 | 0.8 ± 0.45 | 1.4 ± 0.55 | 1.6 ± 0.55 |
| | 21st Day | 1.2 ± 0.45 | 0.2 ± 0.45 | 0.8 ± 0.45 | 1.2 ± 0.45 |
| Heat | 7th Day | 3.0 ± 0.00 | 3.0 ± 0.00 | 2.8 ± 0.45 | 3.0 ± 0.00 |
| | 14th Day | 1.4 ± 0.55 | 1.0 ± 0.71 | 1.0 ± 0.71 | 1.2 ± 0.45 |
| | 21st Day | 0.6 ± 0.55 | 0.4 ± 0.55 | 0.6 ± 0.55 | 0.6 ± 0.55 |
| Limping | 7th Day | 2.8 ± 0.45 | 2.8 ± 0.45 | 3.0 ± 0.00 | 2.8 ± 0.45 |
| | 14th Day | 1.4 ± 0.55 | 0.6 ± 0.55 | 1.2 ± 0.45 | 1.3 ± 0.55 |
| | 21st Day | 0.8 ± 0.45 | 0.2 ± 0.45 | 0.6 ± 0.55 | 0.6 ± 0.55 |
| Total Score | 7th Day | 11.6 ± 0.89 | 11.6 ± 0.89 | 11.6 ± 0.89 | 11.6 ± 0.55 |
| | 14th Day | 5.6 ± 0.55 | 3.4 ± 0.55 | 5.0 ± 1.22 | 5.8 ± 1.1 |
| | 21st Day | 3.2 ± 0.45 | 1.2 ± 0.84 | 2.6 ± 1.14 | 3.4 ± 0.55 |
| Max. Effect during Treatment | | 51.7% | 70.7% | 56.9% | 50.0% |
| Total Treatment Effect | | 72.4% | 89.7% | 77.6% | 70.7% |
| Healing Effect upon Discontinuation of Treatment | | 42.9% | 64.7% | 48.0% | 41.4% |

As is apparent from Table 6, the liposome compositions containing the dibenzo-p-dioxin derivative according to the present invention exhibited much higher efficacy than the non-liposomic external-use composition containing the same dibenzo-p-dioxin derivative in the maximum treatment effect during treatment, total treatment effect, and healing effect upon discontinuation of treatment.

In particular, the SUV type liposome composition had the greatest effects, among the other liposome compositions (MLV, LUV) and the non-liposomic external-use composition. Furthermore, when comparing the liposome composition containing 0.5 wt % of sample 14 with the non-liposomic external-use composition containing 1.5 wt % of sample 14, the liposome composition having an active ingredient concentration of ⅓ has been shown to manifest superior effects. Hence, it was confirmed that the composition containing the dibenzo-p-dioxin derivative according to the present invention is much more effective when used with liposome in treating arthritis via skin absorption.

Experimental Example 4

Clinical Effects of Liposome Composition Containing Dibenzo-p-Dioxin Derivative According to the Present Invention on Treating Degenerative Arthritis The effects of the soybean lecithin SUV liposome compositions (including 0.5 wt % of sample 14) prepared in 1 of Experimental example 3 were evaluated in treating patients suffering from degenerative arthritis. As a control (vehicle), a composition was prepared in the same manner as in 1 of Experimental Example 3 for preparing the soybean lecithin SUV liposome composition, with the exception that sample 14 was not added.

74 patients diagnosed with degenerative knee osteoarthritis were selected and randomly divided into two groups (liposome composition group (n=37); vehicle group (n=37)), and the above composition was applied to the skin of the affected area of each patient in a sufficient amount (0.5~2 mL) two times (morning and evening) per day for 4 weeks. After 4 weeks and 8 weeks, the degree of arthritis was evaluated using "WOMAC arthritis index". The WOMAC (Western Ontario and McMaster Universities) arthritis index was determined by 24 items (each item was scored between 0~4) comprising five questionnaires for pain, two questionnaires for stiffness, and seventeen questionnaires for physical function.

70 patients out of the selected total 74 patients participated in the test to the end, and had the age range of 32~81, and were 64% female (n=47) and 36% male (n=27). On the other hand, 4 patients in the vehicle group discontinued the test because there were no effects, and all of the patients of the soybean lecithin SUV liposome composition group participated in the test to the end. The average values and changes of each group before the test (0 week), after 4 and 8 weeks are shown in Table 7 below.

TABLE 7

| WOMAC Index | | Vehicle (n = 33) | Soybean Lecithin SUV Liposome Composition (n = 37) |
|---|---|---|---|
| Pain | 0 week | 10.6 | 10.5 |
| | 4 weeks | 8.3 | 5.7 |
| | 8 weeks | 10.5 | 4.8 |
| | 4-week Change (%) | −21.7 | −45.7 |
| | 8-week Change (%) | −0.9 | −54.3 |
| | Change after Discontinuation of Treatment (%) | 26.5 | −15.8 |
| Stiffness | 0 week | 4.0 | 4.9 |
| | 4 weeks | 3.2 | 2.4 |
| | 8 weeks | 4.1 | 2.0 |
| | 4-week Change (%) | −20.0 | −51.0 |
| | 8-week Change (%) | 2.5 | −59.2 |
| | Change after Discontinuation of Treatment (%) | 28.1 | −16.7 |
| Physical Function | 0 week | 45.2 | 45.1 |
| | 4 weeks | 38.3 | 25.6 |
| | 8 weeks | 43.3 | 19.3 |
| | 4-week Change (%) | −15.3 | −43.2 |
| | 8-week Change (%) | −4.2 | −57.2 |
| | Change after Discontinuation of Treatment (%) | 13.1 | −24.6 |
| Total Score | 0 week | 59.8 | 60.5 |
| | 4 weeks | 49.8 | 33.7 |
| | 8 weeks | 57.9 | 26.1 |
| | 4-week Change (%) | −16.7 | −44.3 |
| | 8-week Change (%) | −3.2 | −56.9 |
| | Change after Discontinuation of Treatment (%) | 16.3 | −22.6 |

As is apparent from Table 7, the liposome compositions containing the dibenzo-p-dioxin derivative according to the present invention can be seen to be more effective in treating degenerative arthritis, compared to drugs reported in the literature (Can. Med. Assoc. J. 171, 333-338 (2004); Scand J. Rheumatol 30, 11-18 (2001)). In particular, when evaluated 4 weeks after the treatment was discontinued, the vehicle group returned to its original conditions but the composition group according to the present invention continued to show the effects of improvement. Thus, the composition according to the present invention alleviated the symptoms of arthritis and attained superior fundamental healing effects. Furthermore, when the composition according to the present invention was used, neither skin irritation nor other side effects were exhibited.

In the case of anti-inflammatory drugs which are presently widely available, improvement in the symptoms was not reported upon discontinuation of the treatment, regardless of oral administration or skin application. Compared to the conventional drugs, the composition according to the present invention can provide outstanding effects that improve symptoms of tissue that is under stress from arthritis and also that reverse the arthritis process itself. As well, there is no concern about gastrointestinal bleeding and cardiovascular disease, which are side effects of internal-use drugs, and also no concern about skin irritation due to the use of patches.

Experimental Example 5

Clinical Effects of Liposome Composition Containing Dibenzo-p-Dioxin Derivative According to the Present Invention on Treating Rheumatoid Arthritis and Other Arthralgia The effects of the soybean lecithin SUV liposome compositions (including 0.5 wt % of sample 14) prepared in 1 of Experimental Example 3 were evaluated when used to treat patients suffering from rheumatoid arthritis and other arthralgia.

22 patients diagnosed with rheumatoid arthritis, and 27 patients suffering from (other arthralgia) not rheumatoid arthritis but exhibiting pain in the finger joints and hip joints except for the knee joint were separately selected, and the above composition was applied in a sufficient amount (0.5~2 mL) two times (morning and evening) per day for 4 weeks to the affected skin of each patient. Before the test and after 4 weeks and 8 weeks, pain (by VAS (Visual Analogue Scale of pain); the current symptom measured by relative length to the length corresponding to the maximum symptom measured by a 100 mm ruler) and PGA (Patient's Global Assessment; the whole evaluation of disease in which the patient feels) were evaluated.

All of the selected 49 patients participated in the test to the end, among which 22 patients affected by rheumatoid arthritis were in the age range of 23~56, and included 10 females and 12 males. The 27 patients suffering from other arthralgia were in the age range of 43~77 and included 18 females and 9 males. The average values and changes before the test (0 week) and after 4 weeks and 8 weeks are shown in Table 8 below.

TABLE 8

| VAS | | Rheumatoid Arthritis (n = 22) | Other Arthralgia (n = 27) |
|---|---|---|---|
| Pain (mm) | 0 week | 63.3 | 52.2 |
| | 4 weeks | 49.1 | 36.3 |
| | 8 weeks | 42.3 | 29.5 |
| | 4-week Change (%) | −22.4 | −30.5 |
| | 8-week Change (%) | −33.2 | −43.5 |
| | Change after Discontinuation of Treatment (%) | −13.8 | −18.7 |
| PGA (mm) | 0 week | 60.8 | 54.3 |
| | 4 weeks | 46.7 | 33.7 |
| | 8 weeks | 40.1 | 27.5 |
| | 4-week Change (%) | −23.2 | −37.9 |
| | 8-week Change (%) | −34.0 | −49.4 |
| | Change after Discontinuation of Treatment (%) | −14.1 | −18.4 |

As is apparent from Table 8, the liposome compositions containing the dibenzo-p-dioxin derivative according to the present invention not only exhibited superior effects in treating rheumatoid arthritis but also exhibited the improvement effects when evaluated 4 weeks after the treatment was discontinued. Furthermore, the compositions according to the present invention manifested superior effects in terms of alleviating and healing other arthralgia symptoms in the finger joints, hip joints, and shoulder joints. During the test, neither skin irritation nor other side effects were shown upon application of the compositions according to the present invention.

INDUSTRIAL APPLICABILITY

According to the present invention, a dibenzo-p-dioxin derivative is very effective in inhibiting NF-kB and AP-1 activity, and can alleviate symptoms of degenerative arthritis and rheumatoid arthritis without irritating the skin or causing side effects and also can continue to exhibit improvement effects for a considerable period of time even after discontinuation of treatment. Furthermore, by containing the dibenzo-p-dioxin derivative in liposomes, the composition according to the present invention can be much more effective in treating arthritis via absorption through skin, and thereby can be useful in treating degenerative arthritis and rheumatoid arthritis.

What is claimed is:

1. A method of treating degenerative arthritis or rheumatoid arthritis in a mammal, the method comprising:
   applying a medicament to a skin of the mammal in need of such treatment, the medicament comprising a pharmaceutically acceptable carrier and at least one composition using three or more compounds represented by Formulas 1 to 7 and 10:

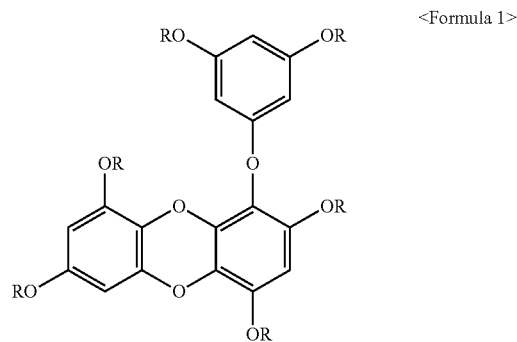

<Formula 1>

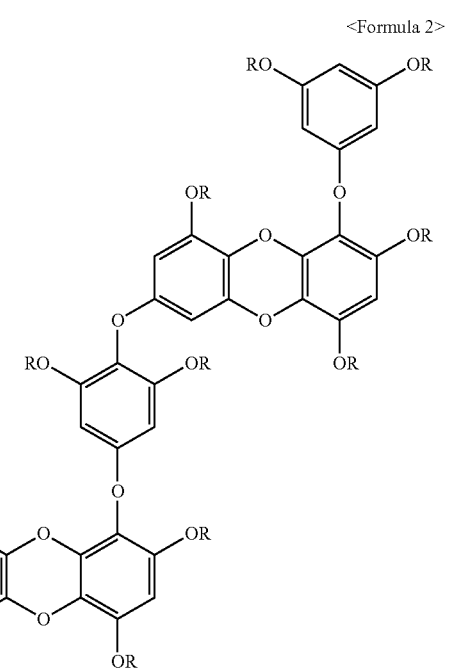

<Formula 2>

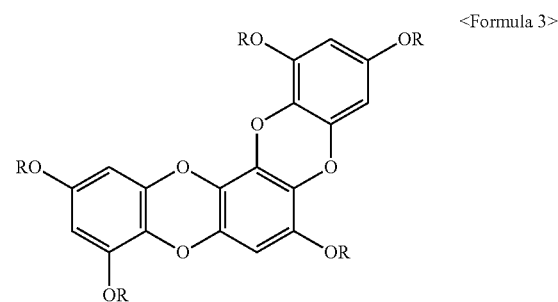

<Formula 3>

-continued

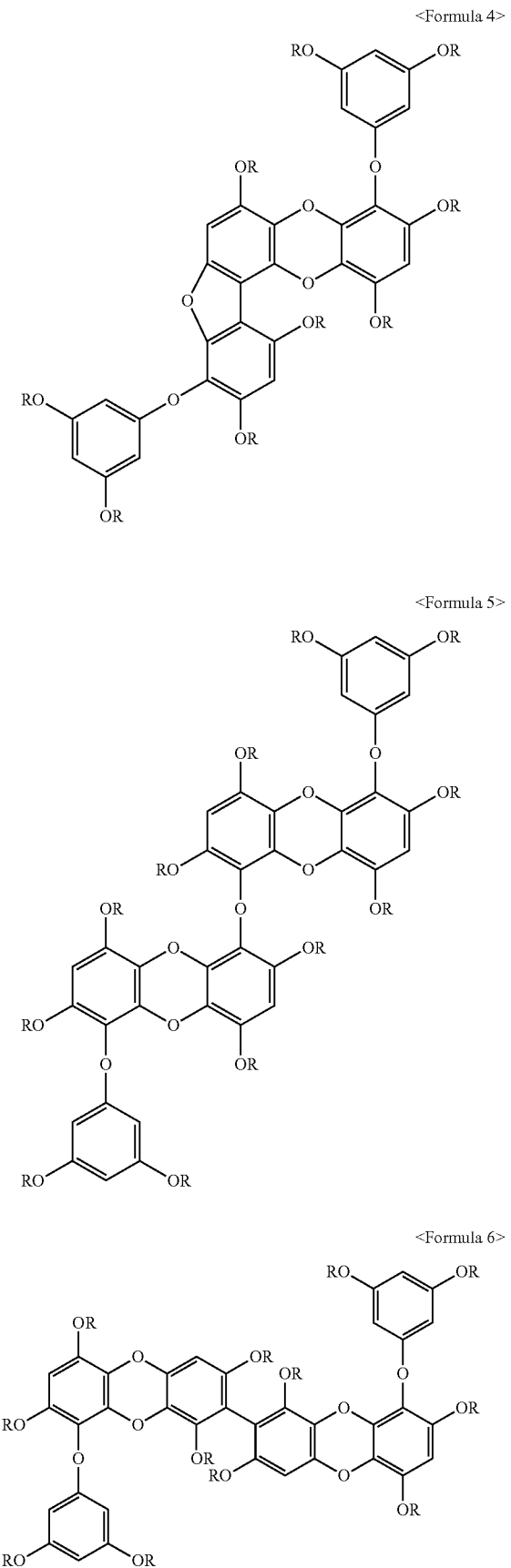

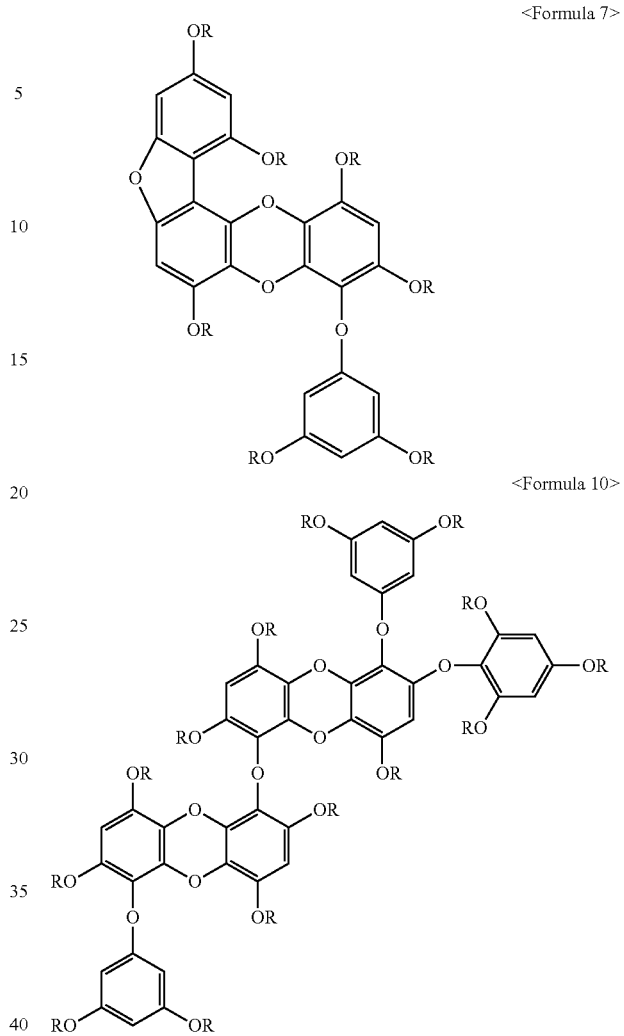

wherein the at least one composition is selected from the group consisting of:

a first composition comprising 60% of the compound of Formula 2 (R=H), 25% of the compound of Formula 3 (R=H), and 15% of the compound of Formula 4 (R=H) with respect to the total weight thereof, a second composition comprising 70% of the compound of Formula 4 (R=H), 8% of the compound of Formula 5 (R=H), and 22% of the compound of Formula 6 (R=H) with respect to the total weight thereof, a third composition comprising 10% of the compound of Formula 4 (R=H), 80% of the compound of Formula 10 (R=H), and 10% of the compound of Formula 7 (R=H) with respect to the total weight thereof, and a fourth composition comprising 3% of the compound of Formula 1 (R=H), 37% of the compound of Formula 2 (R=H), 4% of the compound of Formula 3 (R=H), 6% of the compound of Formula 4 (R=H), 25% of the compound of Formula 5 (R=H), and 25% of the compound of Formula 6 (R=H) with respect to the total weight thereof.

2. The method according to claim 1, wherein the total weight of the at least one composition ranges from 0.2 to 2.0 wt % of the total weight of the medicament.

3. The method according to claim 1, wherein the total weight of the at least one composition ranges from 0.5 to 1.5 wt % of the total weight of the medicament.

4. The method according to claim 1, wherein the medicament is in a form selected from the group consisting of an ointment, a lotion, a cream, a gel, a skin emulsion, a skin suspension, a patch, and a spray.

5. The method according to claim 1, wherein the medicament further comprises a liposome, wherein the at least one composition is contained in the liposome.

6. The method according to claim 5, wherein the liposome comprises multi-lamella vesicles.

7. The method according to claim 5, wherein the liposome comprises unilamella vesicles.

8. The method according to claim 1, wherein the compounds inhibit NF-kB activity or AP-1 activity in cells of the mammal.

* * * * *